United States Patent [19]
Cutie

[11] Patent Number: 6,129,905
[45] Date of Patent: Oct. 10, 2000

[54] AEROSOL FORMULATIONS CONTAINING A SUGAR AS A DISPERSANT

[75] Inventor: Anthony J. Cutie, Bridgewater, N.J.

[73] Assignee: Aeropharm Technology, Inc.

[21] Appl. No.: 08/910,712

[22] Filed: Aug. 13, 1997

Related U.S. Application Data

[63] Continuation-in-part of application No. 08/840,577, Apr. 21, 1997, which is a continuation-in-part of application No. 08/843,811, Apr. 21, 1997.

[51] Int. Cl.$^7$ .................................................... A61L 9/04
[52] U.S. Cl. ........................................ 424/45; 222/402
[58] Field of Search ...................... 424/46, 45; 222/402

[56] References Cited

U.S. PATENT DOCUMENTS

| | | | |
|---|---|---|---|
| 2,868,691 | 1/1959 | Porush et al. . | |
| 2,885,427 | 5/1959 | Ruh et al. | 260/653.7 |
| 3,261,748 | 7/1966 | Larsen | 167/52 |
| 4,129,603 | 12/1978 | Bell | 260/653 |
| 4,174,295 | 11/1979 | Bargigia et al. | 252/305 |
| 5,126,123 | 6/1992 | Johnson | 424/45 |
| 5,182,097 | 1/1993 | Byron et al. | 424/45 |
| 5,190,029 | 3/1993 | Byron et al. . | |
| 5,225,183 | 7/1993 | Purewal et al. | 424/46 |
| 5,254,330 | 10/1993 | Ganderton et al. | 424/45 |
| 5,376,386 | 12/1994 | Ganderton et al. | 424/45 |
| 5,439,670 | 8/1995 | Purewal et al. . | |
| 5,474,759 | 12/1995 | Fassberg et al. | 424/45 |
| 5,492,688 | 2/1996 | Byron et al. | 424/46 |
| 5,569,450 | 10/1996 | Duan et al. . | |
| 5,605,674 | 2/1997 | Purewal et al. | 424/45 |
| 5,607,662 | 3/1997 | Baskeyfield et al. . | |
| 5,612,053 | 3/1997 | Baichwal et al. | 424/440 |
| 5,653,962 | 8/1997 | Akehurst et al. . | |
| 5,658,549 | 8/1997 | Akehurst et al. . | |
| 5,674,471 | 10/1997 | Akehurst et al. . | |
| 5,674,472 | 10/1997 | Akehurst et al. . | |
| 5,676,929 | 10/1997 | Akehurst et al. . | |
| 5,676,931 | 10/1997 | Adjei et al. . | |
| 5,683,676 | 11/1997 | Akehurst et al. . | |
| 5,683,677 | 11/1997 | Purewall et al. . | |
| 5,688,782 | 11/1997 | Neale et al. . | |
| 5,695,743 | 12/1997 | Purewal et al. . | |
| 5,720,940 | 2/1998 | Purewal et al. . | |
| 5,725,841 | 3/1998 | Duan et al. . | |
| 5,736,124 | 4/1998 | Akehurst et al. . | |
| 5,744,123 | 4/1998 | Akehurst et al. . | |

FOREIGN PATENT DOCUMENTS

| | | |
|---|---|---|
| 2046093 | 11/1980 | United Kingdom . |
| 93/11745 | 4/1992 | WIPO . |
| 92/22287 | 8/1992 | WIPO . |
| 95/17195 | 11/1994 | WIPO . |

OTHER PUBLICATIONS

Bower et al. (1996). J. Pharm. Pharmacol. 48(4): 342–346.
Kemp et al. (1997). Am. Allergy Asthma Immunol (US) 79(4): 322–326.
New Scientist, pp. 56–59, May 26, 1988.
Manufacturing Chemist, p. 3, Jun. 1988.
Organic Chemicals Department, E.I. Du Pont de Nemocers & Co., Research Disclosure, p. 70, Oct. 1977.
Rev. Int. Froid., vol. 11, pp. 389–392 (1988).
Aerosol Age, pp. 32–43 (1988).
Saunders, "Handbook of Aerosol Technology" 2nd ed. pp. 30–35, 166–167, and 232–233, Von Nostrand Reinhold Co. (1979).
DuPont Update "Fluorocarbon/Ozone", published by DuPont, Willington, DE (Mar. 1987).
Dictionnaire Vidal, 55th ed. pp. 547–548, O.V.P. Paris (1979).

*Primary Examiner*—Thurman K. Page
*Assistant Examiner*—S. Howard
*Attorney, Agent, or Firm*—Frommer Lawrence & Haug LLP

[57] ABSTRACT

Aerosol formulations for mucosal and/or topical administration containing one or more drugs and a sugar as a dispersant in a pharmaceutically acceptable propellant, are disclosed. Metered dose inhalers suitable for delivering such formulations are also disclosed.

25 Claims, No Drawings

AEROSOL FORMULATIONS CONTAINING A SUGAR AS A DISPERSANT

CROSS-REFERENCE TO RELATED APPLICATIONS

This application is a continuation-in-part of copending U.S. application Ser. No. 08/840,577, entitled "Environmentally Safe Flunisolide Aerosol Formulations for Oral Inhalation," filed Apr. 21, 1997 and a continuation-in-part of copending U.S. application Ser. No. 08/843,811, entitled "Environmentally Safe Triamcinolone Acetonide Aerosol Formulations for Oral Inhalation," filed Apr. 21, 1997, the contents of which are incorporated herein by reference.

FIELD OF THE INVENTION

This invention relates to aerosol formulations for mucosal and topical administration of a drug and, more particularly, to such formulations which contain a hydrocarbon, a chlorofluorofluorocarbon, and/or a hydrofluorocarbon as propellants.

BACKGROUND OF THE INVENTION

Drugs for treating respiratory disorders are frequently administered in oral aerosol formulations. One widely used method for dispensing such an aerosol drug formulation involves making a formulation of the drug in a liquified gas known as a propellant. The drug may be dissolved or suspended in the propellant, or in a combination slurry-solution.

The formulation is dispensed by actuation of a dose metering valve affixed to the container the valve being designed to consistently release a fixed, predetermined amount of the drug formulation upon each activation. As the formulation is forced from the container through the dose metering valve by the high vapor pressure of the propellant, the propellant rapidly vaporizes, leaving a fast-moving cloud of very fine particles or droplets of the drug formulation. This cloud is then directed into the mouth of the patient. Concurrently with the activation of the aerosol dose metering valve, the patient inhales the drug formulation particles into the lungs. Systems for dispensing drugs in this way are known as metered dose inhalers (MDIs).

Chlorofluorocarbons (CFCs) have been used extensively as propellants in drug formulations that are delivered to patients via an MDI. However, recent scientific evidence suggests that CFCs damage the Earth's ozone layer. It is believed that ozone blocks harmful ultraviolet rays and that depletion of the ozone layer will result in the incidence of skin cancer. As a result, steps have been taken to reduce CFC production and usage, and recent recommendations have been made that CFC production be virtually discontinued by the end of this century. Until recently, however, few propellant systems have been discovered which are suitable alternatives to the use of CFCs in MDIs.

The nonchlorinated propellants 1,1,1,2-tetrafluoroethane, also known as hydrofluorocarbon (HFC) 134a, and 1,1,1,2,3,3,3-heptafluoropropane, also known as HFC 227, are among the leading candidates for replacement of the ozone-damaging CFC propellants. However, the substitution of an HFC propellant for the CFC propellants in MDI formulations is not straightforward. There are drug solubility, drug stability and deliverability problems as well as particle size issues which must be addressed when substituting propellants in an MDI formulation. MDIs contain drugs which are dissolved or suspended as micronized particles, propellants in the form of liquified gases, and surface active compounds, or "surfactants," of a type and in a concentration suitable for suspension or dissolution of the drug. Surfactants are included in the formulation to improve particle dispersibility, prevent deaggregation and improve valve function by virtue of its lubricating properties. In some solution formulations, a co-solvent may be added to enhance drug dissolution, although this practice may have the disadvantage of decreasing the fraction of the metered dose which may be inhaled and contributing to particle size growth.

HFC 134a, or 1,1,1,2-tetrafluoroethane (the names will be used interchangeably herein) is nonflammable, has low toxicity and has vapor pressure suitable for use in aerosols. However, HFC 134a is a very poor solvent which fails to dissolve or adequately disperse commonly used surfactants such as sorbitan trioleate, sorbitan monooleate, lecithins and oleic acid in useful concentrations without the aid of a co-solvent.

Similarly, HFC 227, or 1,1,1,2,3,3,3-heptafluropropane (the names will be used interchangeably herein) is nonflammable, has low toxicity and has a vapor pressure suitable for use in aerosols. However, the polarity and solubility of HFC 227 differ from those of commonly used CFC propellants, and many commonly used surfactants are not soluble or are poorly dispersible in HFC 227.

Thus, there remains a need for a method for aiding in the incorporation, dispersion and solubilization of drugs and excipients in aerosol formulations utilizing hydrofluorocarbon propellants such as HFC 134a and HFC 227.

Numerous attempts have been made to formulate aerosols for oral inhalation using non-ozone depleting propellants. However, these formulations generally require the addition of surfactants, polar cosolvents or other adjuvants, and some require the additional manufacturing step of precoating the drug particles with a surfactant prior to dispersal in the propellant.

For example, U.S. Pat. No. 5,225,183 to Purewal et al. discloses MDI formulations which include HFC 134a, a surface active agent, and an adjuvant compound having a higher polarity than HFC 134a. The inclusion of a higher polarity compound in the formulation is said to be critical to the stability and performance of the MDI formulation. The surface active agent is used to stabilize the formulation and lubricate the valve components.

U.S. Pat. No. 5,492,688 to Byron et al. relates to MDI formulations which utilize HFC 134a as the propellant and include a polar surfactant for suspending, solubilizing, wetting and emulsifying the drug constituent and lubricating the valve components of the MDI.

U.S. Pat. No. 5,182,097 to Byron et al. relates to aerosol formulations consisting of 1,1,1,2-tetrafluoroethane, a drug and oleic acid as a surfactant to aid in dispersing the drug in the propellant.

International Application Publication No. WO91/04011 relates to medicinal aerosol formulations in which the micronized drug particles are pre-coated with a surfactant prior to dispersal in 1,1,1,2-tetrafluoroethane.

U.S. Pat. No. 5,612,053 to Baichwal et al. relates to respirable dry powder formulations comprising controlled release particles of a cohesive composite of a drug and a carrier, wherein the carrier is a natural polysaccharide gum added as a filler.

U.S. Pat. No. 5,607,662 to Baskeyfield et al. is directed to a non-pressurized dry powder inhalation composition comprising a medicament and a particulate polysaccharide entrapped flavoring agent, suitable for use in a non-pressurized device.

U.S. Pat. Nos. 5,254,330 and 5,376,386 to Ganderton et al. relate to carriers suitable for use in dry powder inhalant compositions in which the carrier is a saccharide capable of physically absorbing a drug.

But Baichwal et al., Baskeyfield et al. and Ganderton et al. are silent as to the use of beta lactose in the presence of a propellant for use in a pressurized metered dose inhaler or continuous spray aerosol.

It has now been surprisingly found that the use of micronized beta lactose, when formulating pressurized and non-pressurized metered dose inhalers and continuous spray aerosols intended for delivery either on mucous membranes or topically, aids in the incorporation, dispersion and solubilization of drugs and excipients in HFC, hydrocarbon or CFC propellants, and combinations thereof.

SUMMARY OF THE INVENTION

This invention relates to an aerosol formulation for mucosal or topical administration of a medicament which comprises a therapeutically effective amount of a drug, a sugar and a propellant selected from the group consisting of a hydrocarbon, a chlorofluorcarbon, a hydrofluorocarbon and a mixture thereof. Preferably the sugar is lactose. Most preferably the sugar is beta-lactose.

In a preferred embodiment, the sugar has a particle size less than 10 microns. In a more preferred embodiment, the sugar has a particle size less than 5 microns. In a most preferred embodiment, the sugar has a particle size less than 2 microns.

This invention also relates to a metered dose inhaler suitable for delivering such an aerosol formulation. The metered dose inhaler comprises a container capable of withstanding the vapor pressure of the propellant used, and an aerosol formulation comprising a therapeutically effective amount of a drug, a propellant selected from the group consisting of a hydrocarbon, a chlorofluorocarbon, a hydrofluorocarbon, and a mixture thereof, and a sugar. The container is closed with a metering valve having a gasket.

DETAILED DESCRIPTION OF THE INVENTION

The present invention provides an aerosol formulation for mucosal or topical administration comprising a therapeutically effective amount of at least one drug (active), a sugar and optionally one or more pharmaceutically acceptable excipients, dispersed in a pharmaceutically acceptable propellant or mixture of such propellants. In a preferred embodiment, the propellant comprises at least one hydrofluorocarbon propellant.

Formulations of the present invention are suitable for use in pressurized and non-pressurized metered dose inhalers and continuous spray aerosols intended for delivery either onto mucous membranes (e.g., respiratory airways, nasal passageways, sublingually, etc.) or topically. The formulations of the present invention may be suspensions, deaggregated slurries or solutions.

The sugar acts as a solid diluent/dispersant to aid in the incorporation of the dispersion of or solubilization of actives and excipients in hydrocarbon propellants (e.g. propane, butane, etc.), CFC propellants (e.g., P-11, P-12, P-114, etc.), and HFC propellants (e.g., HFC 134a, HFC 227, etc.), and combinations thereof. The sugar may be mixed as a dry discrete spray dried or micronized powder or micronized with the drug and, optionally, one or more excipients, or added separately before or after adding the actives or excipients, as a facilitator in forming the dispersion. The inventive formulations can be formulated with or without the aid of cosolvents or liquid or solid surfactants.

Sugars suitable for use in the present invention include lactose, mannitol, sorbitol, fructose and galactose. In a preferred embodiment, the sugar is lactose. In a most preferred embodiment, the sugar is beta-lactose.

The sugar may also act as a density modifier to either minimize or maximize settling rates or dispersion floc volumes of the bulk compounded formulation, any intermediate step or the final product's formulation.

The sugar is capable of (1) facilitating the dispersion of the drug(s) and/or excipients; (2) stabilizing formulations, either physically, chemically, or both; (3) facilitating the transfer of aerosolized drug; (4) facilitating the drug's micronization and/or deaggregation or manipulating other in vitro qualities of the drug or formulation containing the same; (5) acting as a respiratory sensitizer or desensitizer of drug surface interactions at topical and/or mucosal surfaces; and (6) acting as a density modifier.

Drugs which may be administered via the inventive formulations include: flunisolide, flunisolide hemihydrate, cromolyn sodium, isoproterenol sulfate, metaproterenol sulfate, ipratropium bromide, terbutaline sulfate, beclomethasone, beclomethasone dipropionate, beclomethasone monopropionate, albuterol, dexamethasone, dexamethasone sodium phosphate, isoproterenol HCl, phenylephrine bitartrate, epinephrine, epinephrine bitartrate, ergotamine tartrate, triamcinolone acetonide, budesonide, fluticoside, salmeterol xinafoate, perbuterol sulfate, and pharmaceutically acceptable salts and derivatives of any of these drugs. Mixtures of two or more drugs may also be administered via the formulations of the present invention. This list is intended to illustrate preferred embodiments, and it is by no means intended to limit the effective scope of the claims.

Propellants are generally present in the formulations of the present invention in an amount of at least 90% by weight of the formulation, and preferably greater than 95% by weight of the formulation. Most preferably, the propellants are present in an amount from about 97.5% to about 99.75% by weight of the formulation.

The concentration of the drug(s) in the formulations of the present inventions depends upon the desired dosage, but is generally between about 0.005% and about 5% of the formulation by weight, and preferably comprises from about 0.01% to about 2% by weight of the formulation. More preferably, the drug(s) comprise from about 0.15% to about 1.5% by weight of the formulation. Most preferably, the drug(s) comprise from about 0.3% to about 0.9% by weight of the formulation.

The concentration of the sugar in the present formulations should be approximately 1/100 to 1/10 that of the drug; the sugar is generally present in an amount about 0.015% and about 0.15% of the formulation by weight. Preferably the sugar comprises from about 0.03% to about 0.09% by weight of the formulation.

The particle size of the sugar should be no greater than 10 microns diameter, since larger particles are not transported to the airways effectively. Preferably substantially all of the particles should be less than 5 microns in diameter. Most preferably substantially all of the particles should be less than about 2 microns in diameter. There is no lower limit on particle size except that which will be readily absorbed and retained on or in body tissues. When particles of less than about one-half micron in diameter are administered by inhalation, they tend to be exhaled by the patient.

In formulations of the present invention where ethanol is present, it comprises less than 5% of the formulation. Preferably ethanol is present in an amount from about 0.5% to about 3% by weight of the formulation. More preferably, ethanol is present in an amount from about 1% to about 2% by weight of the formulation.

The particle size of the micronized drug should be no greater than 100 microns in diameter, since larger particles may clog the value or orifice of the container. Preferably, substantially all of the particles should be less than 25 microns in diameter. More preferably, substantially all of the particles should be less than about 10 microns in diameter. Most preferably, substantially all of the particles should be from about 0.5 to about 8 microns in diameter.

Flavoring or taste-masking agents optionally may be added to the compositions of the instant invention. Suitable flavoring agents will be known to the skilled artisan. Preferred flavoring agents include menthol and peppermint oil and combinations thereof. The flavoring agent is preferably present in an amount effective to mask the taste of the drug when an aerosolized dose of the formulation is inhaled orally. In general, amounts of about 0.01% to about 5.0% by weight of the composition are used with amounts of about 0.05% to about 1.0% by weight being preferred.

In addition to flavoring agents, other excipients may be added to an aerosol formulation to improve drug delivery, shelf life and patient acceptance. Such optional excipients include, but are not limited to, buffers, surfactants, colorants, antioxidants and chemical stabilizers. Such excipients must be non-reactive with the drug and relatively non-toxic. The vapor pressure of the excipients should be such that the overall formula vapor pressure should be below 80 psig at room temperature.

If a surfactant is used, typically it is present in an amount from about $\frac{1}{100}$ to $\frac{1}{10}$ that of the drug. Preferred surfactants include oleic acid and oleyl alcohol.

The formulations of the present invention may be filled into conventional aerosol containers using conventional filling equipment well known to those skilled in the art. All of the propellant may be charged to the compounding tank at once, or a portion of the propellant may be charged as part of the concentrate with the remainder being charged as a final step, NEAT.

Depending on the particular application the container may be charged with a predetermined quantity of formulation for single or multiple dosing. Typically, the container is sized for multiple-dosing, and, therefore, it is very important that the formulation delivered is substantially uniform for each dosing. Preferably, the container is charged with a sufficient quantity of the formulation for 10–800 mcg drug/actuation.

The chemical and physical stability and the pharmaceutical acceptability of the aerosol formulations of the present invention may be determined by conventional analytical techniques well known to those skilled in the art. These include particle size measurement, drug active total assay, degradation assay, drug delivery per actuation, weight delivery per actuation, component/formulation compatibility and extractables, etc. The skilled artisan will be able to make appropriate adjustments to compensate for processing parameters and the corresponding physical and thermodynamic properties of the propellants at those conditions.

The advantages of the present invention can be further appreciated by reference to the following examples. These examples are intended to illustrate preferred embodiments and are by no means intended to limit the effective scope of the claims. All percentages are by weight unless otherwise specified.

EXAMPLE 1

| Ingredient | Quantity per Can |
|---|---|
| Flunisolide anhydrous, micronized | 0.0330 g[1] |
| β-lactose | 0.0033 g |
| HFC 134a | 7.2200 g |

[1]Includes a 10% overcharge to assure 500 mcg/actuation delivery from the valve, 120 theoretical actuations to ensure the delivery of 100 metered actuations.

A pressure vessel was sealed, cooled to −40° C. and pressurized to 35 psig. When the set point temperature and pressure was achieved, the entire amount of propellant was charged to the compounding tank by way of a precooling heat exchanger set to cool the propellant to −40° C. at the appropriate flow rate. Mixing of the tank contents was begun, and continued throughout the entire compounding and filling/manufacturing process. While homogenizing the contents of the pressure vessel, first the entire amount of beta-lactose and then the entire amount of drug active were charged to the vessel. The temperature and pressure were then adjusted to −10° C. and 100 psig. When the set point temperature and pressure had been achieved, the vessel contents were homogenized for an additional 10 minutes. The tank contents were then recirculated through a pressure filler and the temperature of the concentrate was allowed to equilibrate with the filling equipment for 10 minutes. A 50 mcl metered dose valve was vacuum sealed onto a 20 mm aluminum can by applying vacuum with a vacuum sealing device, then the valve was crimped onto the can while under vacuum. The full dose was pressure filled through the valve using pressure filling equipment.

EXAMPLE 2

| Ingredient | Quantity per can |
|---|---|
| Triamcinolone acetonide | 0.0634 g[1] |
| β-Lactose | 0.0063 g |
| HFC 227 | 20.2400 g |

[1]Includes a 10% overcharge to assure 200 mcg/actuation delivery from the valve, 240 theoretical actuations to ensure the delivery of 200 metered actuations.

The formula was prepared by the method of Example 1.

EXAMPLE 3

| Ingredient | Quantity per can |
|---|---|
| Triamcinolone acetonide | 0.634 g[1] |
| β-Lactose | 0.0063 g |

-continued

| Ingredient | Quantity per can |
|---|---|
| Ethanol, 200 proof | 0.2020 g |
| HFC 227 | 19.9500 g |

[1]Includes a 10% overcharge to assure 200 mcg/actuation delivery from the valve, 240 theoretical actuations to ensure the delivery of 200 metered actuations.

The entire amount of ethanol is charged to an appropriately sized pressure vessel. Mixing of the tank contents is begun, and continued throughout the entire compounding and filling/manufacturing process. While homogenizing the contents of the pressure vessel, first the entire amount of beta-lactose and then the entire amount of drug active are charged to the vessel. The pressure vessel is sealed, cooled to −40° C. and pressurized to 35 psig. When the set point temperature and pressure is achieved, the entire amount of propellant is charged to the compounding tank by way of a precooling heat exchanger set to cool the propellant to −40° C. at the appropriate flow rate. The temperature and pressure are then adjusted to −10° C. and 100 psig. When the set point temperature and pressure have been achieved, the vessel contents are homogenized for an additional 10 minutes. The tank contents are then recirculated through a pressure filler and the temperature of the concentrate is allowed to equilibrate with the filling equipment for 10 minutes. A 50 mcl metered dose valve is vacuum sealed onto a can by applying vacuum with a vacuum sealing device, then the valve is crimped onto the can while under vacuum. The full dose is pressure filled through the valve using pressure filling equipment.

EXAMPLE 4

| Ingredient | Quantity per can |
|---|---|
| Triamcinolone acetonide | 0.0633 g[1] |
| β-Lactose | 0.0063 g |
| HFC 134a | 9.4300 g |
| HFC 227 | 9.4300 g |

[1]Includes a 10% overcharge to assure 200 mcg/actuation delivery from the valve, 240 theoretical actuations to ensure the delivery of 200 metered actuations.

A pressure vessel is sealed, cooled to −40° C. and pressurized to 35 psig. When the set point temperature and pressure is achieved, the entire amount of HFC 134a followed by the entire amount of HFC 227 is charged to the compounding tank by way of a precooling heat exchanger set to cool the propellant to −40° C. at the appropriate flow rate. Mixing of the tank contents is begun, and continues throughout the entire compounding and filling/manufacturing process. While homogenizing the contents of the pressure vessel, first the entire amount of beta-lactose and then the entire amount of drug active is charged to the vessel. The temperature and pressure are then adjusted to −10° C. and 100 psig. When the set point temperature and pressure have been achieved, the vessel contents are homogenized for an additional 10 minutes. The tank contents are then recirculated through a pressure filler and the temperature of the concentrate is allowed to equilibrate with the filling equipment for 10 minutes. A 50 mcl metered dose valve is vacuum sealed onto a 21 ml can by applying vacuum with a vacuum sealing device, then the valve is crimped onto the can while under vacuum. The full dose is pressure filled through the valve using pressure filling equipment.

Alternatively, the two propellants may be preblended prior to changing to the compounding tank.

EXAMPLE 5

| Ingredient | Quantity per can |
|---|---|
| Triamcinolone acetonide | 0.0634 g[1] |
| β-Lactose | 0.0063 g |
| Ethanol, 200 proof | 0.1900 g |
| HFC 134a | 9.3000 g |
| HFC 227 | 9.3000 g |

[1]Includes a 10% overcharge to assure 200 mcg/actuation delivery from the valve, 240 theoretical actuations to ensure the delivery of 200 metered actuations.

The formula is prepared by the method of Example 3.

EXAMPLE 6

| Ingredient | Quantity per can |
|---|---|
| Flunisolide anhydrous | 0.0660 g[1] |
| β-Lactose | 0.0066 g |
| HFC 227 | 8.3900 g |

[1]Includes a 10% overcharge to assure 500 mcg/actuation delivery from the valve, 120 theoretical actuations to ensure the delivery of 100 metered actuations.

The formula is prepared by the method of Example 1.

EXAMPLE 7

| Ingredient | Quantity per can |
|---|---|
| Flunisolide anhydrous | 0.0660 g[1] |
| β-Lactose | 0.0066 g |
| Ethanol, 200 proof | 0.0840 g |
| HFC 227 | 8.2700 g |

[1]Includes a 10% overcharge to assure 500 mcg/actuation delivery from the valve, 120 theoretical actuations to ensure the delivery of 100 metered actuationg.

The formula is prepared by the method of Example 3.

EXAMPLE 8

| Ingredient | Quantity per can |
|---|---|
| Flunisolide anhydrous | 0.0660 g[1] |
| β-Lactose | 0.0066 g |
| HFC 134a | 3.9100 g |
| HFC 227 | 3.9100 g |

[1]Includes a 10% overcharge to assure 500 mcg/actuation delivery from the valve, 120 theoretical actuations to ensure the delivery of 100 metered actuations.

The formula is prepared by the method of Example 4.

EXAMPLE 9

| Ingredient | Quantity per can |
| --- | --- |
| Flunisolide anhydrous | 0.0660 g[1] |
| β-Lactose | 0.0066 g |
| Ethanol, 200 proof | 0.0800 g |
| HFC 134a | 3.8500 g |
| HFC 227 | 3.8500 g |

[1]Includes a 10% overcharge to assure 500 mcg/actuation delivery from the valve, 120 theoretical actuations to ensure the delivery of 100 metered actuations.

The formula is prepared by the method of Example 3.

EXAMPLE 10

| Ingredient | Quantity per can |
| --- | --- |
| Flunisolide anhydrous | 0.0660 g[1] |
| β-Lactose | 0.0066 g |
| Menthol | 0.0085 g |
| HFC 227 | 8.3800 g |

[1]Includes a 10% overcharge to assure 500 mcg/actuation delivery from the valve, 120 theoretical actuations to ensure the delivery of 100 metered actuations.

A pressure vessel is sealed, cooled to −40° C. and pressurized to 35 psig. When the set point temperature and pressure is achieved, the entire amount of propellant is charged to the compounding tank by way of a precooling heat exchanger set to cool the propellant to −40° C. at the appropriate flow rate. Mixing of the tank contents is begun, and continues throughout the entire compounding and filling/manufacturing process. While homogenizing the contents of the pressure vessel, first the entire amount of beta-lactose and then the entire amount of drug active are charged to the vessel. The temperature and pressure are adjusted to −10° C. and 100 psig. The menthol is then added to the mix. When the set point temperature and pressure have been achieved, the vessel contents are homogenized for an additional 10 minutes. The tank contents are then recirculated through a pressure filler and the temperature of the concentrate is allowed to equilibrate with the filling equipment for 10 minutes. A metered dose valve is vacuum sealed onto a 20 mm aluminum can by applying vacuum with a vacuum sealing device, then the valve is crimped onto the can while under vacuum. The full dose is pressure filled through the valve using pressure filling equipment.

EXAMPLE 11

| Ingredient | Quantity per can |
| --- | --- |
| Flunisolide anhydrous | 0.0660 g |
| β-Lactose | 0.0066 g |
| Menthol | 0.0084 g |
| Ethanol, 200 proof | 0.0840 g |
| HFC 227 | 8.2600 g |

[1]Includes a 10% overcharge to assure 500 mcg/actuation delivery from the valve, 120 theoretical actuations to ensure the delivery of 100 metered actuations.

The entire amount of ethanol is charged to an appropriately sized pressure vessel. Mixing of the tank contents is begun, and continued throughout the entire compounding and filling/manufacturing process. While homogenizing the contents of the pressure vessel, first the entire amount of beta-lactose and then the entire amount of drug active are charged to the vessel. The pressure vessel is sealed, cooled to −40° C. and pressurized to 35 psig. When the set point temperature and pressure is achieved, the entire amount of propellant is charged to the compounding tank by way of a precooling heat exchanger set to cool the propellant to −40° C. at the appropriate flow rate. The temperature and pressure are adjusted to −10° C. and 100 psig. The menthol is then added to the mix. When the set point temperature and pressure have been achieved, the vessel contents are homogenized for an additional 10 minutes. The tank contents are then recirculated through a pressure filler and the temperature of the concentrate is allowed to equilibrate with the filling equipment for 10 minutes. A 50 mcl metered dose valve is vacuum sealed onto a can by applying vacuum with a vacuum sealing device, then the valve is crimped onto the can while under vacuum. The full dose is pressure filled through the valve using pressure filling the equipment.

EXAMPLE 12

| Ingredient | Quantity per can |
| --- | --- |
| Flunisolide anhydrous | 0.0661 g |
| β-Lactose | 0.0066 g |
| Menthol | 0.0080 g |
| HFC 134a | 3.9100 g |
| HFC 227 | 3.9100 g |

[1]Includes a 10% overcharge to assure 500 mcg/actuation delivery from the valve, 120 theoretical actuations to ensure the delivery of 100 metered actuations.

The formula is prepared by the method of Example 10.

EXAMPLE 13

| Ingredient | Quantity per can |
| --- | --- |
| Funisolide anhydrous | 0.0660 g[1] |
| β-Lactose | 0.0066 g |
| Menthol | 0.0080 g |
| Ethanol, 200 proof | 0.0800 g |
| HFA 134a | 3.8500 g |
| HFA 227 | 3.8500 g |

[1]Includes a 10% overcharge to assure 500 mcg/actuation delivery from the valve, 120 theoretical actuations to ensure the delivery of 100 metered actuations.

The formula is prepared by the method of Example 11.

EXAMPLE 14

| Ingredient | Quantity per can |
| --- | --- |
| Flunisolide anhydrous | 0.0660 g[1] |
| β-Lactose | 0.0066 g |
| Oleic acid | 0.0066 g |
| HFC 227 | 8.3800 g |

[1]Includes a 10% overcharge to assure 500 mcg/actuation delivery from the valve, 120 theoretical actuations to ensure the delivery of 100 metered actuations.

A pressure vessel is sealed, cooled to −40° C. and pressurized to 35 psig. When the set point temperature and pressure is achieved, the entire amount of propellant is charged to the compounding tank by way of a precooling heat exchanger set to cool the propellant to −40° C. at the appropriate flow rate. Mixing of the tank contents is begun, and continues throughout the entire compounding and filling/manufacturing process. While homogenizing the contents of the pressure vessel, first the entire amount of beta-lactose and then the entire amount of drug active are charged to the vessel. The temperature and pressure are adjusted to −10° C. and 100 psig. The oleic acid is then added to the mix. When the set point temperature and pressure have been achieved, the vessel contents are homogenized for an additional 10 minutes. The tank contents are then recirculated through a pressure filler and the temperature of the concentrate is allowed to equilibrate with the filling equipment for 10 minutes. A metered dose valve is vacuum sealed onto a 20 mm aluminum can by applying vacuum with a vacuum sealing device, then the valve is crimped onto the can while under vacuum. The full dose is pressure filled through the valve using pressure filling equipment.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

What is claimed is:

1. A pressurized aerosol formulation comprising:
    a) a therapeutically effective amount of at least one drug;
    b) a hydrofluorocarbon propellant;
    c) optionally at least one excipient; and
    c) a sugar with a particle size no greater than 10 microns in diameter present in an amount effective to facilitate the dispersion of the drug and, if present, excipient.

2. The formulation of claim 1 wherein said sugar is selected from the group consisting of lactose, mannitol, sorbitol, fructose and galactose.

3. The formulation of claim 2 wherein said sugar is beta-lactose.

4. The formulation of claim 1, wherein said at least one drug is selected from the group consisting of flunisolide, flunisolide hemihydrate, cromolyn sodium, isoproterenol sulfate, metaproterenol sulfate, ipratropium bromide, terbutaline sulfate, beclomethasone, beclomethasone dipropionate, beclomethasone monopropionate, albuterol, dexamethasone, dexamethasone sodium phosphate, isoproterenol HCl, phenylephrine bitartrate, epinephrine, epinephrine bitartrate, ergotamine tartrate, triamcinolone acetonide, budesonide, fluticoside, salmeterol xinafoate, perbuterol sulfate, and pharmaceutically acceptable salts and derivatives thereof, and combinations thereof.

5. The formulation of claim 1, wherein said drug is present in an amount from about 0.01% to about 2% by weight of the formulation.

6. The formulation of claim 5, wherein said drug is present in an amount from about 0.15% to about 1.5% by weight of the formulation.

7. The formulation of claim 6, wherein said drug is present in an amount from about 0.30% to about 0.90% by weight of the formulation.

8. The formulation of claim 1, wherein said sugar is present in an amount from about 0.01% to about 2% by weight of the formulation.

9. The formulation of claim 8, wherein said sugar is present in an amount from 0.015% to about 0.15% by weight of the formulation.

10. The formulation of claim 9, wherein said sugar is present in an amount from 0.03% to about 0.09% of the formulation.

11. The formulation of claim 1, wherein said propellant is HFC 134a.

12. The formulation of claim 1, wherein said propellant is HFC 227.

13. The formulation of claim 1, wherein said propellant is a mixture of HFC 134a and HFC 227.

14. The formulation of claim 1, wherein said drug has a particle size less than 10 microns.

15. The formulation of claim 1, wherein said drug has a particle size from about 0.5 to about 8 microns.

16. The formulation of claim 1, wherein said sugar has a particle size less than 5 microns.

17. The formulation of claim 16, wherein said sugar has a particle size less than 2 microns.

18. A pressurized metered dose inhaler suitable for delivering an aerosol formulation which comprises:

a) a container capable of withstanding the vapor pressure of the propellant used, said container being closed with a metering valve having a gasket; and b) a pressurized an aerosol formulation contained in said container, said formulation comprising:

(1) a therapeutically effective amount of at least one drug;

(2) a hydrofluorocarbon propellant;

(3) optionally at least one excipient; and (4) a sugar with a particle size no greater than 10 microns in diameter present in an amount effective to facilitate the dispersion of the drug and, if present, the excipient.

19. The metered dose inhaler of claim 18 wherein said sugar is selected from the group consisting of lactose, mannitol, sorbitol, fructose and galactose.

20. In a process for preparing an aerosol formulation comprising at least one drug, a hydrofluorocarbon propellant and optionally at least one excipient, the improvement which comprises adding a sugar with a particle size no greater than 10 microns in diameter present in an amount effective to facilitate the dispersion said drug and optional excipient.

21. A method of preparing a dispersed aerosol formulation comprising at least one drug, a hydrofluorocarbon propellant; and optionally at least one excipient, said method comprises adding a sugar with a particle size no greater than 10 microns in diameter present in an amount effective to facilitate the dispersion of said drug and optional excipient.

22. A method of preparing a dispersed aerosol formulation comprising at least one drug, a propellant selected from the group consisting of a hydrocarbon, hydrofluorocarbon and a mixture thereof, and optionally at least one excipient, said method comprises adding a sugar with a particle size no greater than 10 microns in diameter present in an amount effective to facilitate the dispersion of said drug and optional excipient.

23. The method according to claim 22, wherein the aerosol formulation is a pressurized aerosol formulation.

24. A pressurized aerosol formulation comprising:

(a) a therapeutically effective amount of at least one drug;

(b) a hydrofluorocarbon propellant;

(c) optionally at least one excipient; and (d) a sugar with a particle size no greater than 10 microns in diameter present in an amount effective to facilitate the dispersion of the drug and, if present, excipient, wherein the sugar is selected from the group consisting of lactose and galactose.

25. A method for dispersing an aerosol formulation comprising at least one drug, a hydrofluorocarbon propellant and a mixture thereof and, optionally, at least one excipient, the improvement which comprises adding a sugar with a particle size no greater than 10 microns in diameter present in an amount effective to facilitate the dispersion of said drug and optional excipient.

* * * * *